United States Patent [19]

Gilbert et al.

[11] Patent Number: 5,116,847

[45] Date of Patent: May 26, 1992

[54] USE OF LOPERAMIDE AND RELATED COMPOUNDS FOR TREATMENT OF RESPIRATORY DISEASE SYMPTOMS

[75] Inventors: Sheri A. Gilbert, Cincinnati; Haruko Mizoguchi, Fairfield; Robert P. Charest, Forest Park; Timothy P. O'Neill, Wyoming; Ronald L. Smith, West Chester, all of Ohio

[73] Assignee: The Procter & Gamble Company, Cincinnati, Ohio

[21] Appl. No.: 645,855

[22] Filed: Jan. 25, 1991

[51] Int. Cl.⁵ .......................................... A61K 31/445
[52] U.S. Cl. .................................. 514/327; 514/849; 514/853
[58] Field of Search ......................................... 514/327

[56] References Cited

U.S. PATENT DOCUMENTS 3,714,159  1/1973  Janssen et al. .................. 260/247.1
4,880,813  11/1989  Frost .................................. 514/282

FOREIGN PATENT DOCUMENTS

87/02586  5/1987  PCT Int'l Appl.

OTHER PUBLICATIONS

Chemical Abstracts 82:106345z.
"5450. Loperamide", The Merck Index, 11th Edition, S. Budavari, ed., p. 876.
Physicians' Desk Reference for Nonprescription Drugs, 12th Ed. (1990), E. R. Barnhardt, pub., p. 599.
"Drug Compendium", Comprehensive Medicinal Chemistry, vol. 6 (1990), C. Hansch, P. E. Sammes, J. B. Taylor & C. J. Drayton, eds., Pergamon Press, N.Y., pp. 628-629.
Niemegeers, C. J. E., F. Awouters, F. M. Lenaerts, K. S. K. Artois & J. Vermeire, "Antidiarrheal Specificity and Safety of the N-Oxide of Loperamide (R 58 425) in Rats", Drug Development Research, vol. 8 (1986), pp. 279-286.
Mackerer, C. R., G. A. Clay & E. Z. Dajani, "Loperamide Binding to Opiate Receptor Sites of Brain and Myenteric Plexus", Journal of Pharmacology and Experimental Therapeutics, vol. 199, No. 1 (1976), pp. 131-140.
Stahl, K. D., W. Van Bever, P. Janssen & E. J. Simon, "Receptor Affinity and Pharmacological Potency of a Series of Narcotic Analgesic, Anti-Diarrheal and Neuroleptic Drugs", European Journal of Pharmacology, vol. 46 (1977), pp. 199-205.
Wuster, M. & A. Herz, "Opiate Agonist Action of Antidiarrheal Agents In Vitro and In Vivo—Findings in Support for Selective Action", Naunyn-Schmiedeberg's Archives of Pharmacology, vol. 301 (1978), pp. 187-194.
Giagnoni, G., L. Casiraghi, R. Senini, L. Revel, D. Parolaro, M. Sala & E. Gori, "Loperamide: Evidence of Interaction with $\mu$ and delta Opioid Receptors", Life Sciences, vol. 33, Suppl. 1 (1983), pp. 315-318.
Mudge, A. W., S. E. Leeman & G. D. Fischbach, "Enkephalin Inhibits Release of Substance P from Sensory Neurons in Culture and Decreases Action Potential Duration", Proceedings of the National Academy of Science, USA, vol. 76, No. 1 (Jan. 1979), pp. 526-530.
Frossard, N. & P. J. Barnes, "$\mu$-Opioid Receptors Modulate Non-cholinergic Constrictor Nerves in Guinea–Pig Airways", European Journal of Pharmacology, vol. 141 (1987), pp. 519-522.
Burleigh, D. E., "Opioid and Non-opioid Actions of Loperamide on Cholinergic Nerve Function in Human Isolated Colon", European Journal of Pharmacology, vol. 152 (1988), pp. 39-46.
Belvisi, M. G., D. F. Rogers & P. J. Barnes, "Neurogenic Plasma Extravasation: Inhibition by Morphine in Guinea Pig Airways In Vivo", Journal of Applied Physiology, vol. 66 (1989), pp. 268-272.
Matran, R., C.-R. Martling & J. M. Lundberg, "Inhibition of Cholinergic and Non-adrenergic, Non-cholinergic Bronchoconstriction in the Guinea Pig Mediated by Neuropeptide Y and $\alpha_2$-adrenoceptors and Opiate Receptors", European Journal of Pharmacology, vol. 163 (1989), pp. 15-23.
Balkovetz, D. F., Y. Miyamoto, C. Tiruppathi, V. B. Mahesh, F. H. Leibach & V. Ganapathy, "Inhibition of Brush-border Membrane $Na^+-H^+$ Exchanger by Loperamide", Journal of Pharmacology and Experimental Therapeutics, vol. 243, No. 1 (Oct. 1987), pp. 150-154.
Beubler, E. & P. Badhri, "Comparison of the Antisecretory Effects of Loperamide and Loperamide Oxide in the Jejunum and the Colon of Rats In-vivo", Journal of Pharmaceutics and Pharmacology, vol. 42 (1990), pp. 689-692.
Chang, E. B., D. R. Brown, N. S. Wang & M. Field, "Secretagogue-induced Changes in Membrane Calcium Permeability in Chicken and Chincilla Ileal Mucosa. Selective Inhibition by Loperamide", Journal of Clinical Investigation, vol. 78, No. 1 (Jul., 1986), pp. 281-287.
Haag, K., R. Lubcke, H. Knauf, E. Berger & W. Gerok, "Determination of Rheogenic Ion Transport in Rat Proximal Colon In Vivo", Pflugers Arch., vol. 405, Suppl. 1 (1985), pp. S67-S70.
Hantz, E., A. Cao, R. S. Phadke & E. Taillandier, "The Effect of Loperamide on the Thermal Behavior of Dimyristoylphosphatidylcholine Large Unilamellar Vesicles", Chemistry and Physics of Lipids (Ireland), vol. 51, No. 2 (Oct. 1989), pp. 78-82.
Hardcastle, J., P. T. Hardcastle & J. Cookson, "Inhibi- (List continued on next page.)

Primary Examiner—Leonard Schenkman
Attorney, Agent, or Firm—Milton B. Graff, IV; Jerry J. Yetter; Richard C. Witte

[57] ABSTRACT

The subject invention involves compositions and methods of using loperamide and related compounds for treatment of symptoms associated with respiratory diseases.

20 Claims, No Drawings

OTHER PUBLICATIONS tory Actions of Loperamide on Absorptive Processes in Rat Small Intestine", Gut, vol. 27, No. 6 (Jun. 1986), pp. 686–694.

Hardcastle, J., P. T. Hardcastle & J. Goldhill, "The Effect of Loperamide Oxide on Prostaglandin-Stimulated Fluid Transport in Rat Small Intestine", Journal of Pharmaceutics and Pharmacology, vol. 42, No. 5 (May, 1990), pp. 364–366.

Hardcastle, J., P. T. Hardcastle, N. W. Read & J. S. Redfern, "The Action of Loperamide in Inhibiting Prostaglandin-induced Intestinal Secretion in the Rat", British Journal of Pharmacology, vol. 74, No. 3 (Nov. 1981), pp. 563–569.

Hughes, S., N. B. Higgs & L. A. Turnberg, "Antidiarrheal Activity of Loperamide: Studies of its Influence on Ion Transport Across Rabbit Ileal Mucosa In Vitro", Gut, vol. 23, No. 11 (Nov. 1982), pp. 974–979.

Kachur, J. F., D. W. Morgan & T. S. Gaginella, "Effect of Dextromethorphan on Guinea Pig Ileal Contractility In Vitro: Comparison with Levomethorphan, Loperamide and Codeine", Journal of Pharmacology and Experimental Therapeutics, vol. 239, No. 3 (Dec. 1986), pp. 661–667.

Knauf, H. & K. Haag, "Modelling of Colonic Cl$^-$ and K$^+$ Transport Under Resting and Secreting Conditions", Pflugers Arch., vol. 407, Supplement 2 (1986), pp. S85–S89.

Marcais-Collado, H., G. Uchida, J. Costentin, J. C. Schwartz & J. M. Lecompte, "Naloxone-reversible Antidiarrheal Effects of Enkephalinase Inhibitors", European Journal of Pharmacology, vol. 144, No. 2 (Dec. 1, 1987), pp. 125–132.

VanNueten, J. M., P. A. J. Janssen & J. Fontaine, "Loperamide, a Novel Type of Antidiarrheal Agent. Part 3: In Vitro Studies on the Peristaltic Reflex and Other Experiments on Isolated Tissues", Arznneimittelforschung, vol. 24, No. 10 (Oct. 1974), pp. 1641–1645.

Marsboom, R., V. Herin, A. Verstraeten, R. Vandesteene & J. Fransen, "Loperamide, a Novel Type of Antidiarrheal Agent. Part 4: Studies on Subacute and Chronic Toxicity and the Effect on Reproductive Processes in Rats, Dogs and Rabbits", Arzneimittelforschung, vol. 24, No. 10 (Oct. 1974), pp. 1645–1649.

Megans, A. A., L. L. Canters, F. H. Awouters & C. J. Niemegeers, "Is In Vivo Dissociation Between the Antipropulsive and Antidiarrheal Properties of Opioids in Rats Related to Gut Selectivity?", Arch. Int. Pharmacodyn., vol. 298 (Mar.–Apr., 1989), pp. 220–229.

Megens, A. A., L. L. Canters, F. H. Awouters & C. J. Neimegeers, "Normalization of Small Intestinal Propulsion with Loperamide-like Antidiarrheals in Rats", European Journal of Pharmacology, vol. 17, (1990), pp. 357–364.

Mellstrand, T., "Loperamide—An Opiate Receptor Agonist with Gastrointestinal Motility Effects", Scand. J. Gastroenterol. Suppl., vol. 130 (1987), pp. 65–66.

Miller, R. J., D. R. Brown, E. B. Chang & D. D. Friel, "The Pharmacological Modification of Secretory Responses", Ciba Found. Symp., vol. 112 (1985), pp. 155–174.

Nakayama, S., T. Yamasato & M. Mitzutani, "Effects of Loperamide on the Motility of the Isolated Intestine in Guinea Pigs, Rats and Dogs", Jap. J. Smooth Muscle Res., vol. 13, No. 2 (Jun., 1977), pp. 69–74.

Niemegeers, C. J., F. M. Lenaerts & P. A. Janssen, "Loperamide, a Novel Type of Antidiarrheal Agent. Part 1: In Vivo Oral Pharmacology and Acute Toxicity. Comparison with Morphine, Codeine, Diphenoxylate and Difenoxine", Arzneimittelforschung, vol. 24, No. 10 (Oct. 1974), pp. 1633–1636.

Niemegeers, C. J., F. M. Lenaerts & P. A. Janssen, "Loperamide, a Novel Type of Antidiarrheal Agent. Part 2: In Vivo Parenteral Pharmacology and Acute Toxicity in Mice. Comparison with Morphine, Codeine, and Diphenoxylate", Arzneimittelforschung, vol. 24, No. 10 (Oct. 1974), pp. 1636–1641.

Sandhu, B. K., P. J. Milla & J. T. Harries, "Mechanisms of Action of Loperamide", Scand. J. Gastroenterol. Suppl., vol. 84 (1983), pp. 85–92.

Stahl, K. D., W. van Bever, P. Janssen & E. J. Simon, "Receptor Affinity and Pharmacological Potency of a Series of Narcotic Analgesic, Anti-diarrheal and Neuroleptic Drugs", European Journal of Pharmacology, vol. 46, No. 3 (Dec. 1, 1977), pp. 199–205.

Stoll, R., H. Stern, H. Ruppin & W. Domschke, "Effect of Two Potent Calmodiun Antagonists on Calcium Transport of Brush Border and Basolateral Vesicles for Human Duodenum", Aliment. Pharmacol. Ther., vol. 1, No. 5 (1987), pp. 415–424, (Abstract only).

Stoll, R., H. Ruppin & W. Domschke, "Calmodulin-mediated Effects of Loperamide on Chloride Transport by Brush Border Membrane Vesicles from Human Ileum", Gastroenterology, vol. 95, No. 1 (Jul. 1988), pp. 69–76.

Turnberg, L. A., "Antisecretory Activity of Opiates In Vitro and In Vivo in Man", Scand. J. Gastroenterol. Suppl., vol. 84 (1983), pp. 79–83.

Turnheim, K., "Antidiarrheal Agents: Tools and Therapeutics", Z. Gastroenterol. (West Germany), vol. 27, No. 2 (Feb. 1989), pp. 112–119.

Verhaeren, E. H., M. J. Dreessen & J. A. Lemli, "Influence of 1,8-Dihydroxyanthraquinone and Loperamide on the Paracellular Permeability Across Colonic Mucosa", Journal of Pharmaceutics and Pharmacology, vol. 33, No. 8 (Aug. 1981), pp. 526–528.

Wehner, F., "Membrane Effects of Loperamide in Absorbing and Secreting Guinea-Pig Gallbladder Epithelium", Naunyn-Schmiedeberg's Archives of Pharmacology, vol. 335, Supplement (1987), p. R45.

Wehner, F., J. M. Winterhager & K. U. Petersen, "Selective Blockage of Cell Membrane K Conductance by an Antisecretory Agent in Guinea-Pig Gallbladder Epithelium", Pflugers Arch. (West Germany), vol. 414, No. 3 (Jul. 1989), pp. 331–339.

Tamaoki, J., N. Sakai, K. Isono & T. Takizawa, "Inhibition by Loperamide of Chloride Transport Across Canine Cultured Tracheal Epithelium", European Journal of Pharmacology, vol. 190 (1990), pp. 255–258.

Saria, A., "Neuroimmune Interactions in the Airways:

(List continued on next page.)

OTHER PUBLICATIONS

Implications for Asthma, Allergy and Other Inflammatory Airway Diseases", Brain, Behavior, and Immunity, vol. 2 (1988), pp. 318–321.

Wolf, G., "New Aspects in the Pathogenesis and Treatment of Hyperreactive Rhinopathy", Laryng. Rhinol. Otol., vol. 67 (1988), pp. 438–445.

Stjarne, P., L. Lundblad, J. M. Lundberg & A. Anggard, "Capsaicin and Nicotine-Sensitive Afferent Neurons and Nasal Secretion in Healthy Human Volunteers and in Patients with Vasomotor Rhinitis", British Journal of Pharmacology, vol. 96 (1989), pp. 693–701.

Geppetti, P., B. M. Fusco, S. Marabini, C. A. Maggi, M. Fanciullaci & F. Sicuteri, "Secretion, Pain and Sneezing Induced by the Application of Capsaicin in the Nasal Mucosa in Man", British Journal of Pharmacology, vol. 93 (1988), pp. 509–514.

USE OF LOPERAMIDE AND RELATED COMPOUNDS FOR TREATMENT OF RESPIRATORY DISEASE SYMPTOMS

TECHNICAL FIELD

The subject invention relates to the use of loperamide and related compounds for the treatment of symptoms such as nasal congestion, runny nose, sneezing, itchy nose, itchy eyes, watery eyes, cough, bronchoconstriction and post-nasal drip. Such symptoms are associated with respiratory diseases such as colds, flu, allergic and vasomotor rhinitis, asthma and bronchitis.

BACKGROUND OF THE INVENTION

Loperamide is an opiate agonist used for the treatment of diarrhea; see "5396. Loperamide", *The Merck Index*, Tenth Edition, M. Windholz, ed., p. 797; and *Physicians' Desk Reference for Nonprescription Drugs*, 11th Ed. (1990), E. R. Barnhart, pub., pp. 593-594. Loperamide is one of a class of compounds disclosed in U.S. Pat. No. 3,714,159 issued to Janssen, Niemegeers, Stokbroekx & Vandenberk on Jan. 30, 1973. Lomeramide N-oxide is disclosed in "Drug Compendium", *Comprehensive Medicinal Chemistry*, Vol. 6 (1990), C. Hansch, P. G. Sammes, J. B. Taylor & C. J. Drayton, eds., Pergamon Press, N.Y., p. 629, and in Niemegeers, C. J. E., F. Awouters, F. M. Lenaerts, K. S. K. Artois & J. Vermeire, "Antidiarrheal Specificity and Safety of the N-Oxide of Loperamide (R 58 425) in Rats", *Drug Development Research*, Vol. 8 (1986), pp. 279-286. The above references are hereby incorporated herein by reference.

Loperamide is similar to other opiate agonists in having binding affinities at mu and delta opiate receptors. See, e.g., Mackerer, C. R., G. A. Clay & E. Z. Dajani, "Loperamide Binding to Opiate Receptor Sites of the Brain and Myenteric Plexus", *Journal of Pharmacology and Experimental Therapeutics*, Vol. 199, No. 1 (1976), pp. 131-140; Stahl, K. D., W. Van Bever, P. Janssen & E. J. Simon, "Receptor Affinity and Pharmacological Potency of a Series of Narcotic Analgesic, Anti-Diarrheal and Neuroleptic Drugs", *European Journal of Pharmacology*, Vol. 46 (1977), pp. 199-205; Wuster, M. & A. Herz, "Opiate Agonist Action of Antidiarrheal Agents In Vitro and In Vivo—Findings in Support for Selective Action", *Naunyn-Schmiedeberg's Archives of Pharmacology*, Vol. 301 (1978), pp. 187-194; and Giagnoni, G., L. Casiraghi, R. Senini, L. Revel, D. Parolaro, M. Sala & E. Gori, "Loperamide: Evidence of Interaction with μ and δ Opioid Receptors", *Life Sciences*, Vol. 33, Suppl. 1 (1983), pp. 315-318. It is generally accepted that mu and/or delta opioid agonists bind to opioid receptors on the presynaptic terminals of peripheral parasympathetic nerves or sensory nerves and inhibit the release of neurotransmitters from these nerve terminals in a number of model systems. See, e.g., Mudge, A. W., S. E. Leeman & G. D. Fischbach, "Enkephaline Inhibits Release of Substance P from Sensory Neurons in Culture and Decreases Action Potential Duration", *Proceedings of the National Academy of Science, USA*, Vol. 76, No. 1 (Jan. 1979), pp. 526-530; Frossard, N. & P. J. Barnes, "μ-Opioid Receptors Modulate Non-cholinergic Constrictor Nerves in Guinea-Pig Airways", *European Journal of Pharmacology*, Vol. 141 (1987), pp. 519-522; Burleigh, D. E., "Opioid and Non-opioid Actions of Loperamide on Cholinergic Nerve Function in Human Isolated Colon", *European Journal of Pharmacology*, Vol. 152 (1988), pp. 39-46; Belvisi, M. G., D. F. Rogers & P. J. Barnes, "Neurogenic Plasma Extravasation: Inhibition by Morphine in Guinea Pig Airways In Vivo", *Journal of Applied Physiology*, Vol. 66 (1989), pp. 268-272; and Matran, R., C.-R. Martling & J. Lundberg, "Inhibition of Cholinergic and Non-adrenergic, Non-cholinergic Bronchoconstriction in the Guinea Pig Mediated by Neuropeptide Y and α2-adrenoceptors and Opiate Receptors", *European Journal of Pharmacology*, Vol. 163 (1989), pp. 15-23. This inhibition is prevented or reversed by the mu and delta selective opioid antagonist naloxone.

References which disclose the biological and chemical activity of loperamide include the following: Balkovetz, D. F., Y. Miyamoto, C. Tiruppathi, V. B. Mahesh, F. H. Leibach & V. Ganapathy, "Inhibition of Brush-border Membrane Na+-H+ Exchanger by Loperamide", *Journal of Pharmacology and Experimental Therapeutics*, Vol. 243, No. 1 (Oct. 1987), pp. 150-154; Beubler, E. & P. Badhri, "Comparison of the Antisecretory Effects of Loperamide and Loperamide Oxide in the Jejunum and the Colon of Rats In-vivo", *J. Pharm. Pharmacol.*, Vol. 42 (1990), pp. 689-692; Chang, E. B., D. R. Brown, N. S. Wang & M. Field, "Secretagogue-induced Changes in Membrane Calcium Permeability in Chicken and Chincilla Ileal Mucosa. Selective Inhibition by Loperamide", *J. Clin. Invest.*, Vol. 78, No. 1 (Jul., 1986), pp. 281-287; Haag, K., R. Lubcke, H. Knauf, E. Berger & W. Gerok, "Determination of Rheogenic Ion Transport in Rat Proximal Colon In Vivo", *Pflugers Arch.*, Vol. 405, Suppl. 1 (1985), pp. S67-S70; Hantz, E., A. Cao, R. S. Phadke & E. Taillandier, "The Effect of Loperamide on the Thermal Behavior of Dimyristoylphosphatidylcholine Large Unilamellar Vesicles", *Chem. Phys. Lipids (Ireland)*, Vol. 51, No. 2 (Oct. 1989), pp. 75-82; Hardcastle, J., P. T. Hardcastle & J. Cookson, "Inhibitory Actions of Loperamide on Absorptive Processes in Rat Small Intestine", *Gut*, Vol. 27, No. 6 (Jun. 1986), pp. 686-694; Hardcastle, J., P. T. Hardcastle & J. Goldhill, "The Effect of Loperamide Oxide on Prostaglandin-Stimulated Fluid Transport in Rat Small Intestine", *J. Pharm. Pharmacol.*, Vol. 42, No. 5 (May, 1990), pp. 364-366; Hardcastle, J., P. T. Hardcastle, N. W. Read & J. S. Redfern, "The Action of Loperamide in Inhibiting Prostaglandin-induced Intestinal Secretion in the Rat", *British Journal of Pharmacology*, Vol. 74, No. 3 (Nov. 1981), pp. 563-569; Hughes, S., N. B. Higgs & L. A. Turnberg, "Antidiarrhoeal Activity of Loperamide: Studies of its Influence on Ion Transport Across Rabbit Ileal Mucosa In Vitro", *Gut*, Vol. 23, No. 11 (Nov. 1982), pp. 974-979; Kachur, J. F., D. W. Morgan & T. S. Gaginella, "Effect of Dextromethorphan on Guinea Pig Ileal Contractility In Vitro: Comparison with Levomethorphan, Loperamide and Codeine", *Journal of Pharmacology and Experimental Therapeutics*, Vol. 239, No. 3 (Dec. 1986), pp. 661-667; Knauf, H. & K. Haag, "Modelling of Colonic Cl− and K+ Transport Under Resting and Secreting Conditions", *Pflugers Arch.*, Vol. 407, Supplement 2 (1986), pp. S85-S89; Marcais-Collado, H., G. Uchida, J. Costentin, J. C. Schwartz & J. M. Lecompte, "Naloxone-reversible Antidiarrheal Effects of Enkephalinase Inhibitors", *European Journal of Pharmacology*, Vol. 144, No. 2 (Dec. 1, 1987), pp. 125-132; Marsboom, R., V. Herin, A. Verstraeten, R. Vandesteene & J. Fransen, "Loperamide, a Novel Type of Antidiarrheal Agent. Part 3: In Vitro Studies on the Peristaltic Reflex and Other Experiments on Isolated Tissues", *Arzneimittelforschung*, Vol. 24, No. 10 (Oct. 1974), pp. 1641-1645; Marsboom, R., V. Herin, A. Verstraeten, R. Vandesteene & J. Fransen, "Loperamide, a Novel Type of Antidiarrheal Agent. Part 4: Studies on Subacute and Chronic Toxicity and the Effect on Reproductive Processes in Rats, Dogs and Rabbits", *Arzneimittelforschung*, Vol. 24, No. 10 (Oct. 1974), pp. 1645-1649; Megens, A. A., L. L. Canters, F. H. Awouters & C. J. Niemegeers, "Is In Vivo Dissociation Between the Antipropulsive and Antidiarrheal Properties of Opioids in Rats Related to Gut Selectivity?", *Arch. Int. Pharmacodyn. Ther.*, Vol. 298 (Mar.-Apr., 1989), pp. 220-229; Megens, A. A., L. L. Canters, F. H. Awouters & C. J. Niemegeers, "Normalization of Small Intestinal Propulsion with Loperamide-like Antidiarrheals in Rats", *European Journal of Pharmacology*, Vol. 178, No. 3 (Mar. 27, 1990), pp. 357-364; Mellstrand, T., "Loperamide—An Opiate Receptor Agonist with Gastrointestinal Motility Effects", *Scand. J. Gastroenterol. Suppl.*, Vol. 130 (1987), pp. 65-66; Miller, R. J., D. R. Brown, E. B. Change & D. D. Friel, "The Pharmacological Modification of Secretory Responses", *Ciba Found. Symp.*, Vol. 112 (1985), pp. 155-174; Nakayama, S., T. Yamasato & M. Mitzutani, "Effects of Loperamide on the Motility of the Isolated Intestine in Guinea Pigs, Rats and Dogs", *Niooon Heikatsukin Gakkai Zasshi*, Vol. 13, No. 2 (Jun., 1977), pp. 69-74; Niemegeers, C. J., F. M. Lenaerts & P. A. Janssen, "Loperamide, a Novel Type of Antidiarrheal Agent. Part 2: In Vivo Parenteral Pharmacology and Acute Toxicity in Mice. Comparison with Morphine, Codeine and Diphenoxylate", *Arzneimittelforschung*, Vol. 24, No. 10 (Oct. 1974), pp. 1636-1641; Niemegeers, C. J., F. M. Lenaerts & P. A. Janssen, "Loperamide, a Novel Type of Antidiarrheal Agent. Part 1: In Vivo Oral Pharmacology and Acute Toxicity. Comparison with Morphine, Codeine, Diphenoxylate and Difenoxine", *Arzneimittelforschung*, Vol. 24, No. 10 (Oct. 1974), pp. 1633-636; Sandhu, B. K., P. J. Milla & J. T. Harries, "Mechanisms of Action of Loperamide", *Scand. J. Gastroenterol. Suppl.*, Vol. 84 (1983), pp. 85-92; Stahl, K. D., W. van Bever, P. Janssen & E. J. Simon, "Receptor Affinity and Pharmacological Potency of a Series of Narcotic Analgesic, Anti-diarrheal and Neuroleptic Drugs", *European Journal of Pharmacology*, Vol. 46, No. 3 (Dec. 1, 1977), pp. 199-205; Stoll, R., H. Stern, H. Ruppin & W. Domschke, "Effect of Two Potent Calmodulin Antagonists on Calcium Transport of Brush Border and Basolateral Vesicles for Human Duodenum", *Ailment. Pharmacol. Ther.*, Vol. 1, No. 5 (1987), pp. 415-424; Stoll, R., H. Ruppin & W. Domschke, "Calmodulin-mediated Effects of Loperamide on Chloride Transport by Brush Border Membrane Vesicles from Human Ileum", *Gastroenterology*, Vol. 95, No. 1 (Jul. 1988), pp. 69-76; Turnberg, L. A., "Antisecretory Activity of Opiates In Vitro and In Vivo in Man", *Scand. J. Gastroenterol. Suppl.*, Vol. 84 (1983), pp. 79-83; Turnheim, K., "Antidiarrheal Agents: Tools and Therapeutic Agents", *Z. Gastroenterol.* (West Germany), Vol. 27, No. 2 (Feb. 1989), pp. 112-119; Verhaeren, E. H., M. J. Dreessen & J. A. Lemli, "Influence of 1,8-Dihydroxyanthraquinone and Loperamide on the Paracellular Permeability Across Colonic Mucosa", *J. Pharm. Pharmacol.*, Vol. 33, No. 8 (Aug. 1981), pp. 526-528; Wehner, F., "Membrane Effects of Loperamide in Absorbing and Secreting Guinea-Pig Gallbladder Epithelium", *Naunyn-Schmiedeberg's Archives of Pharmacology*, Vol. 335, Supplement (1987), p. R45; Wehner, F., J. M. Winterhager & K. U. Peterson, "Selective Blockage of Cell Membrane K Conductance by an Antisecretory Agent in Guinea-Pig Gallbladder Epithelium", *Pfugers Arch.* (West Germany), Vol 414, No. 3 (Jul. 1989), pp. 331-339.

Tamaski, J., N. Sakai, K. Isono & T. Takizawa, "Inhibition by Loperamide of Chloride Transport Across Canine Cultured Tracheal Epithelium", *European Journal of Pharmacology*, Vol. 190 (1990), pp. 255-258, speculates that the inhalation of loperamide could be of value in the treatment of patients with excessive airway surface fluid.

Evidence suggests that sensory C-fiber activation is important in the induction of symptoms associated with rhinitis; see, e.g., Saria, A., "Neuroimmune Interactions in the Airways: Implications for Asthma, Allergy and Other Inflammatory Airway Diseases", *Brain, Behavior, and Immunity*, Vol 2 (1988), pp. 318-321; Wolf, G. "New Aspects in the Pathogenesis and Therapy of Hyperreactive Rhinopathy", *Laryng. Rhinol. Otol.*, Vol 67 (1988), pp. 438-445; and Stjarne, P., L. Lundblad, J. M. Lundberg & A. Anggard, "Capsaicin and Nicotine-Sensitive Afferent Neurons and Nasal Secretion in Healthy Human Volunteers and in Patients with Vasomotor Rhinitis", *British Journal of Pharmacology*, Vol. 96 (1989), pp. 693-710. In respiratory tissue, C-fiber activation causes the local release of inflammatory neuropeptides and also initiates a parasympathetic reflex. Both of these actions produce physiologic changes that can result in the symptoms of rhinorrhea and congestion; see, e.g., Stjarne, et al. and Geppetti, P., B. M. Fusco, S. Marabini, C. A. Maggi, M. Fanciullacci & F. Sicuteri, "Secretion, Pain and Sneezing Induced by the Application of Capsaicin in the Nasal Mucosa in Man", *British Journal of Pharmacology*, Vol. 93 (1988), pp. 509-514.

It has been reported that the opioid antagonist nalmefene is useful for the treatment of rhinitis; see, e.g., U.S. Pat. No. 4,880,813 issued to Frost on Nov. 14, 1989, and PCT Patent Application Publication No. WO 87/02586 of Key Pharmaceuticals, Inc., inventor: Tuttle, published May 7, 1987.

It is an object of the subject invention to provide novel methods for the treatment of rhinitis.

It is further object of the subject invention to provide novel methods for the topical, intranasal treatment of rhinitis.

SUMMARY OF THE INVENTION

The subject invention involves the use of compounds, or N-oxide thereof, or pharmaceutically-acceptable salts thereof, having the structure;

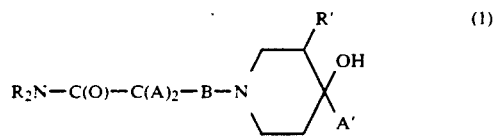

wherein each —R independently selected from hydrogen and lower alkyl, or the two —Rs are conencted to form a cyclic lower alkyl; each —A is independently selected from phenyl and halophenyl; —B— is selected from —CH$_2$CH$_2$— and —CH$_2$CH(CH$_3$)—; —R' is hydrogen or methyl; and —A' is phenyl or substituted phenyl;

for treatment of symptoms associated with respiratory diseases.

DETAILED DESCRIPTION OF THE INVENTION

As used herein, "lower alkyl" means alkyl which is preferably unsubstituted $C_1-C_6$ straight or branched alkyl, preferably saturated, more preferably $C_1-C_4$, more preferably still ethyl, and especially methyl.

As used herein, "lower alkoxy" means —O—lower alkyl.

As used herein, "cyclic lower alkyl" means cyclic alkyl which is preferably unsubstituted $C_3-C_8$, preferably unsaturated, more preferably $C_5-C_6$.

As used herein, "substituted phenyl" means phenyl which is preferably mono-, di- or trisubstituted, more preferably mono-substituted, especially in the 4-position. Preferred phenyl substituents include lower alkyl, lower alkoxy, halo and trifluoromethyl. As used herein, "halophenyl" means substituted phenyl which is substituted with fluoro, chloro, bromo, and/or iodo. Preferred halo substituents are fluoro and chloro.

The subject invention involves a new use of compounds, or N-oxide thereof, or pharmaceutically-acceptable salts thereof, having the structure:

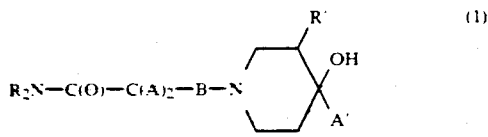

In Structure (1), each —R is independently selected from hydrogen and lower alkyl, or the two —Rs are connected to form a cyclic lower alkyl.

In Structure (1), each —A is independently selected from phenyl or halophenyl; preferred are 4-F-phenyl and especially phenyl.

In Structure (1), —B— is —CH$_2$CH$_2$— or —CH$_2$CH(CH$_3$)—, preferably —CH$_2$CH$_2$—.

In Structure (1), —R' is hydrogen or methyl, preferably hydrogen.

In Structure (1), —A' is phenyl or substituted phenyl; especially preferred is 4-Cl-phenyl.

Preferred salts of the compounds of Structure (1) include hydrochloride, hydrobromide, acetate, citrate, lactate, tartrate, succinate and maleate.

A preferred compound of Structure (1) is loperamide, 4-(4-chlorophenyl)-4-hydroxy-N,N-dimethyl-α,α-diphenyl-1-piperdinebutanamide, or the N-oxide thereof, and especially the hydrochloride salt of loperamide or its N-oxide.

The subject invention involves the use of a safe and effective amount of the above compounds for treatment of symptoms associated with respiratory diseases, such as colds, flu, allergic and vasomotor rhinitis, asthma and bronchitis, of humans and lower animals, especially humans. Such symptoms can include, for example, one or more of nasal congestion, runny nose, sneezing, itchy nose, itchy eyes, watery eyes, cough, broncoconstriction and post-nasal drip. The subject invention particularly involves the treatment with the above compounds of upper respiratory nasal symptoms, such as nasal congestion, runny nose, sneezing, and post-nasal drip. The subject invention also particularly involves the treatment with the above compounds of lower respiratory symptoms, such as bronchoconstriction and cough. Relief of the above symptoms can be achieved by the methods of the subject invention with minimal or no side effects often associated with therapies for such symptoms, such as drowsiness, central nervous system excitation, or rebound congestion. A preferred mode of administering the above compounds in the methods of the subject invention is topical, intranasal administration, e.g., with nose drops, nasal spray or nasal mist inhalation. Another preferred mode of administering the above compounds in the methods of the subject invention is topical, bronchial administration by inhalation of vapor and/or mist or powder. Such modes of topical administration minimize or prevent any gastrointestinal effects of the compounds.

The methods and compositions of the subject invention involve a safe and effective amount of the above compounds. The phrase "safe and effective amount", as used herein for the above compounds or other substances, means an amount of the substance high enough to provide a significant positive modification of the condition to be treated, but low enough to avoid serious side effects (at a reasonable benefit/risk ratio), within the scope of sound medical judgement. A safe and effective amount of the substance will vary with the particular condition being treated, the age and physical condition of the patient being treated, the severity of the condition, the duration of the treatment, the nature of concurrent therapy and like factors.

Each administration of a dose of a composition comprising a compound according to the methods of the subject invention preferably administers a dose within the range of from about 1 μg to about 4 mg of a compound, more preferably from about 20 μg to about 2 mg, more preferably still from about 40 μg to about 1 mg. The frequency of administration of a composition comprising a compound according to the subject invention is preferably from once to about 6 times daily, more preferably from about 2 times to about 4 times daily.

Another aspect of the subject invention is pharmaceutical compositions for topical administration of the above compounds to the eyes, nasal passages and sinuses, or bronchial passages and lungs. Preferred compositions for topical administration to eyes include eye drops. Preferred compositions for topical administration to the nasal passages and sinuses include nasal drops, nasal sprays, and vapors and/or mists for nasal inhalation. Preferred compositions for topical administration to the bronchial passages and lungs include vapors and/or mists or powders for inhalation.

The above topical compositions of the subject invention preferably comprise an above compound at a concentration of from about 0.002% to about 1%, more preferably from about 0.02% to about 0.2%, more preferably still from about 0.05% to about 0.1%. Preferred topical compositions of the subject invention are powder mixtures or aqueous-based solutions or suspensions; especially preferred are aqueous solutions.

Other ingredients which may be incorporated in such compositions include safe and effective amounts of preservatives, e.g., benzalkonium chloride, thimerosal, phenylmercuric acetate; and acidulants, e.g., acetic acid, citric acid, lactic acid, tartaric acid. Such compositions preferably include safe and effective amounts of isotonicity agents, e.g., salts such as sodium chloride; more preferred are non-electrolyte isotonicity agents, e.g., sorbitol, mannitol, lower molecular weight polyethylene glycol.

A particularly preferred ingredient of the compositions of the subject invention is a safe and effective amount of a solubilizing agent. Loperamide and its salts are sparingly soluble in water. A suitable solubilizing agent increases the solubility of loperamide and/or its salts in the aqueous compositions. Such solubilizing agents can also provide isotonicity for the aqueous compositions. Preferred solubilizing agents are modified cyclodextrins, preferably hydroxy-$C_1$-$C_6$ alkyl derivatives, especially hydroxypropyl derivatives. A particularly preferred solubilizing agent is 2-hydroxypropyl-$\beta$-cyclodextrin. Solubilizing agents are preferably present in the compositions of the subject invention at a concentration of from about 0.1% to about 10%, more preferably from about 0.5% to about 5%.

The compositions of the subject invention also may comprise safe and effective amounts of one or more other active drug agents useful for treating the respiratory diseases of interest. Such other active drug agents and typical amounts dosed are disclosed in *Physician's Desk Reference*, 44th Edition (1990), E. R. Barnhardt, publisher, and *Physician's Desk Reference for Nonprescription Drugs*, 11th Edition (1990), E. R. Barnhardt, publisher, both of which are incorporated herein by reference.

The topical nasal compositions of the subject invention may include one or more of the following such other active drug agents: antihistamines, e.g., chlorpheniramine maleate, pyrilamine maleate, diphenhydramine hydrochloride, promethazine hydrochloride, doxylamine succinate, terfenadine, astemizole; decongestants, e.g., pseudoephedrine hydrochloride, phenyl propanolamine hydrochloride, phenylephrine hydrochloride, oxymetazoline hydrochloride, xylometazoline hydrochloride; steroidal anti-inflammatories, e.g., beclomethasone dipropionate, flunisolide; mast cell stabilizers, e.g., cromolyn sodium, nedocromil; anticholinergics, e.g., ipratropium bromide.

The topical bronchial compositions of the subject invention may include one or more of the following such other active drug agents: antitussives, e.g., dextromethorphan base or hydrobromide; bronchodilators, e.g., theophylline, metaproterenol, albuterol; steroidal anti-inflammatories, e.g., beclomethasone; mast cell stabilizers, e.g., cromolyn sodium.

Oral compositions of the subject invention may include one or more of the following such other active drug agents: antihistamines, e.g., chlorpheniramine maleate, pyrilamine maleate, diphenhydramine hydrochloride, promethazine hydrochloride, doxylamine succinate, terfenadine, astemizole; decongestants, e.g., pseudoephedrine hydrochloride, phenylpropanolamine hydrochloride, phenylephrine hydrochloride; antitussives, e.g., dextromethorphan base or hydrobromide; nonsteroidal anti-inflammatories, e.g., aspirin, acetaminophen, ibuprofen, naproxen; expectorants, e.g., guaifenesin; bronchodilators, e.g., theophylline, metaproterenol, albuterol; antibiotics.

Another aspect of the subject invention is a combination of a composition comprising an above compound in a container comprising a means for tophcal application of the composition to the eyes, nasal passages and sinuses, or bronchial passages and lungs. Preferred containers useful in such combinations include those comprising dropper means, spray means, or inhalation mist or powder means.

Containers comprising dropper means are useful for applying, as a liquid, either eye drops or nose drops topically to the eye or nasal passages, respectively. Such containers are well-known and commonly have such dropper means attached permanently or removably to the body of the container so that drops can be administered by inverting the container and/or by squeezing the container (the container being flexible). Another well-known dropper means is attached to a closure for the container and comprises a tube with a small hole in one end, the other end being open and attached to a flexible (e.g., rubber) bulb.

Containers comprising spray means are useful for applying a spray of liquid droplets topically directly to nasal passages. Well-known examples of such containers are flexible plastic containers having a spray nozzle fixedly attached thereto, the spray nozzle being designed for insertion into the nasal opening. When the container is squeezed, solution in the container is forced through the nozzle and emerges as a spray of droplets. Other well-known containers with spray means, e.g. pump sprays or aerosol sprays, can also be used in a similar manner.

Containers comprising inhalation mist means are useful for applying a fine mist or powder topically to nasal passages and/or bronchial passages and lungs. Such inhalers provide a fine mist or powder which can be inhaled either through the nose or the mouth, depending on the design of the inhaler. Inhalers designed for providing a mist or powder to be inhaled through the nose are useful for topical administration of compositions to nasal passages and/or bronchial passages and lungs. Inhalers designed for providing a mist or powder to be inhaled through the mouth are useful for topical administration of compositions to bronchial passages and lungs. Various containers having inhalation mist or powder means as a part of or fixedly attached to the containers are well-known, e.g., squeeze containers, pump containers, and aerosols.

The following non-limiting examples exemplify compositions and methods useful in the subject invention.

EXAMPLE 1

| Intranasal Composition | |
|---|---|
| Ingredient | Amount (weight/volume %) |
| Loperamide hydrochloride, U.S.P. | 0.050 |
| Benzalkonium chloride | 0.020 |
| Thimerosal | 0.002 |
| d-Sorbitol | 5.700 |
| Glycine | 0.380 |
| Purified water | q.s. |

One-fifth ml of the composition of Example 1 is applied as drops from a dropper into each nostril of a patient with nasal congestion. The congestion is substantially diminished.

EXAMPLE 2

| Intranasal Composition | |
|---|---|
| Ingredient | Amount (weight/volume %) |
| Loperamide hydrochloride, U.S.P. | 0.100 |
| Benzalkonium chloride | 0.020 |
| d-Sorbitol | 5.000 |
| Glycine | 0.350 |
| Acetic acid (0.35 M) | 0.075 |

-continued

| Intranasal Composition | |
|---|---|
| Ingredient | Amount (weight/volume %) |
| Purified water | q.s. |

One-tenth ml of the composition of Example 2 is sprayed through a nozzle into each nostril of a patient with a runny nose. Nasal secretion is substantially reduced.

EXAMPLE 3

| Intranasal Composition | |
|---|---|
| Ingredient | Amount (weight/volume %) |
| Loperamide hydrochloride, U.S.P. | 0.200 |
| Benzalkonium chloride | 0.020 |
| 2-Hydroxypropyl-β-cyclodextrin | 5.000 |
| Purified water | q.s. |

One-tenth ml of the composition of Example 3 is sprayed through a nozzle into each nostril of a patient with post-nasal drip. The post-nasal drip substantially ceases.

While particular embodiments of the subject invention have been described, it will be obvious to those skilled in the art that various changes and modifications of the subject invention can be made without departing from the spirit of the scope of the invention. It is intended to cover, in the appended claims, all such modifications that are within the scope of this invention.

What is claimed is:

1. A method of treatment of symptoms associated with respiratory diseases, of humans and lower animals, comprising administration to the human or lower animal safe and effective amount of a compound having the structure:

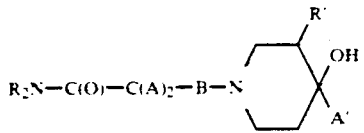

wherein each —R is independently hydrogen or lower alkyl, or the two —Rs are connected to form a cyclic lower alkyl; each —A is independently phenyl or halophenyl; —B— is —CH$_2$CH$_2$— or —CH$_2$CH(CH$_3$)—; —R′ is hydrogen or methyl; and —A′ is phenyl or substituted phenyl;
or N-oxide thereof, or a pharmaceutically-acceptable salt thereof.

2. The method of claim 1 wherein each —R is C$_1$-C$_4$alkyl, and —R′ is hydrogen.

3. The method of claim 2 wherein —A′ is 4-halophenyl.

4. The method of claim 1 wherein the compound is loperamide or N-oxide thereof, or a salt thereof.

5. The method of claim 4 wherein the compound is loperamide hydrochloride.

6. The method of claim 1 wherein a composition comprising the compound is administered to a human, and the quantity of compound administered is from about 1 μg to about 4 mg per dose.

7. The method of claim 4 wherein a composition comprising the compound is administered to a human, and the quantity of compound administered is from about 1 μg to about 4 mg per dose.

8. The method of claim 7 wherein the composition is administered topically, and the quantity of the compound administered is from about 20 μg to about 2 mg per dose.

9. The method of claim 7 wherein the composition is administered topically, intranasally, and the quantity of the compound administered is from about 40 μg to about 1 mg per dose.

10. A composition, for use in the nasal passages and sinuses for treatment of symptoms associated with respiratory diseases, in the form of an aqueous solution comprising:
(a) a safe and effective amount of a compound having the structure:

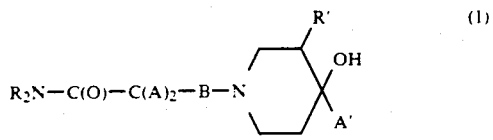

wherein each —R is independently hydrogen or lower alkyl, or the two —Rs are connected to form a cyclic lower alkyl; each —A is independently phenyl or halophenyl; —B— is —CH$_2$CH$_2$— or —CH$_2$CH(CH$_3$)—; —R′ is hydrogen or methyl; and —A′ is phenyl or substituted phenyl;
or N-oxide thereof, or a pharmaceutically-acceptable salt thereof, and
(b) a safe and effective amount of a preservative selected from the group consisting of benzalkonium chloride, thimerosal, and phenylmercuric acetate.

11. The composition of claim 10 wherein the compound is loperamide or a salt thereof, the compound being at a concentration of from about 0.002% to about 1% in the composition.

12. A composition, for treatment of symptoms associated with respiratory diseases, in the form of an aqueous soluton comprising:
(a) a safe and effective amount of loperamide or a salt thereof; and
(b) a safe and effective amount of another drug active selected from the group consisting of antihistamines, decongestants, expectorants, bronchodilators, and antitussives.

13. The composition of claim 12 wherein the other drug active is selected from the group consisting of antitussives and bronchodilators.

14. The composition of claim 12 wherein the other drug active is selected from the group consisting of antihistamines and decongestants.

15. A composition, for treatment of symptoms associated with respiratory diseases, in the form of an aqueous solution comprising:
(a) a safe and effective amount of loperamide or a salt thereof; and
(b) a safe and effective amount of a steroidal or non-steroidal anti-inflammatory drug agent.

16. A composition, for treatment of symptoms asociated with respiratory diseases, in the form of an aqueous solution comprising:
(a) a safe and effective amount of loperamide or a salt thereof; and
(b) a safe and effective amount of an anticholinergic drug agent.

17. A combination comprising:
(a) a container comprising a means for topical application selected from the group consisting of dropper means, spray means and inhalation mist means, the container containing:
(b) a composition, for treatment of symptoms associated with respiratory diseases, in the form of an aqueous solution comprising a safe and effective amount of a compound having the structure:

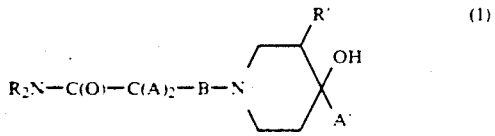

(1)

wherein each —R is independently hydrogen or lower alkyl, or the two —Rs are conencted to form a cyclic lower alkyl; each —A is independently phenyl or halophenyl; —B—is —$CH_2CH_2$—or —$CH_2CH(CH_3)$—; —R' is hydrogen or methyl; and —A' is phenyl or substituted phenyl;

or N-oxide thereof, or a pharmaceutically-acceptable salt thereof.

18. The combination of claim 17 wherein the container comprises a dropper means, and the compound is loperamide or a salt thereof, the compound being at a concentration of from about 0.002% to about 1% in the composition.

19. The combination of claim 17 wherein the container comprises a spray means, and the compound is loperamide or a salt thereof, the compound being at a concentration of from about 0.002% to about 1% in the composition.

20. The combiantion of claim 17 wherein the container comprises an inhalation mist or powder means, and the compound is loperamide or a salt thereof, he compound being at a concentration of from about 0.002% to about 1% in the composition.

* * * * *

UNITED STATES PATENT AND TRADEMARK OFFICE
CERTIFICATE OF CORRECTION

PATENT NO. : 5,116,847
DATED : May 26, 1992
INVENTOR(S) : S.A. Gilbert, H. Mizoguchi, R.P. Charest, T.P. O'Neill and R.L. Smith It is certified that error appears in the above-identified patent and that said Letters Patent is hereby corrected as shown below:

Column 4, line 63 and 64, "connected" should be --connected--.

Column 5, line 39, "-B-is" should be -- -B- is--.

Column 5, line 60-61, "broncoconstriction" should be --bronchoconstriction--.

Column 7, line 46-47, "may, include" should be --may include--.

Column 7, line 61, "tophcal" should be --topical--.

Column 9, line 50, "-B-is" should be -- -B- is--.

Column 9, line 55-56, "$C_1-C_4$alkyl," should be --$C_1-C_4$ alkyl,--.

Column 10, line 28, "-B-is -$CH_2CH_2$-or" should be -- -B- is -$CH_2CH_2$- or--.

Column 10, line 41, "inthe" should be --in the--.

Column 11, line 20, "-B-is -$CH_2CH_2$-or" should be -- -B- is -$CH_2CH_2$- or--.

Column 12, line 17, "and the compound is loperamide or a salt thereof, he" should be --and the compound is loperamide or a salt thereof, the--.

Signed and Sealed this

Eleventh Day of January, 1994

Attest:

BRUCE LEHMAN

Attesting Officer    Commissioner of Patents and Trademarks